United States Patent
Campbell et al.

(10) Patent No.: US 6,613,310 B1
(45) Date of Patent: Sep. 2, 2003

(54) DUAL COMPONENT BIS-BIGUANIDE CONTAINING DENTIFRICE OF IMPROVED STABILITY

(75) Inventors: Thomas S. Campbell, Piscataway, NJ (US); Alexander J. Simone, Somerset, NJ (US); Nuran Nabi, Cranbury, NJ (US); Michael Collins, Hazlet, NJ (US)

(73) Assignee: Colgate Palmolive Company, Piscataway, NJ (US)

( * ) Notice: Subject to any disclaimer, the term of this patent is extended or adjusted under 35 U.S.C. 154(b) by 0 days.

(21) Appl. No.: 10/207,612

(22) Filed: Jul. 29, 2002

(51) Int. Cl.[7] ................................................. A61K 7/16

(52) U.S. Cl. ........................................ 424/54; 424/49

(58) Field of Search ...................................... 424/49–58

(56) References Cited

U.S. PATENT DOCUMENTS

| | | | | |
|---|---|---|---|---|
| 5,855,871 A | * | 1/1999 | Masters et al. | 424/49 |
| 5,958,381 A | * | 9/1999 | Curtis et al. | 424/54 |
| 6,180,089 B1 | * | 1/2001 | Gambogi et al. | 424/52 |
| 6,346,235 B1 | * | 2/2002 | Joziak et al. | 424/52 |

* cited by examiner

*Primary Examiner*—Shep K. Rose
(74) *Attorney, Agent, or Firm*—Paul Shapiro

(57) ABSTRACT

A dual component chlorhexidine dentifrice composition of improved shelf stability in which the first component is a gel containing a bis-biguanide antibacterial agent in which the gel vehicle is thickened with a cellulose polymer and the second component is a paste containing a silica abrasive wherein the bis-biguanide antibacterial agent provides undiminished antiplaque and antigingivitis effect with reduced staining when the physically separated components are combined and mixed upon application to dental tissue.

5 Claims, No Drawings

DUAL COMPONENT BIS-BIGUANIDE CONTAINING DENTIFRICE OF IMPROVED STABILITY

BACKGROUND OF THE INVENTION

1. Field of the Invention

The present invention relates to an oral care composition which contains a bis-biguanide compound effective in the retardation of bacterial plaque accumulation on the teeth and gum diseases such as gingivitis and periodontitis. More particularly, the present invention relates to a dual component dentifrice composition of improved shelf-stability containing a bis-biguanide compound which achieves plaque and gimgivitis reduction with substantially less staining of teeth than normally occurs with bis-biguanide compound containing dentifrices and rinses.

2. The Prior Art

Dental plaque is a soft deposit which forms on teeth and is comprised of an accumulation of bacteria and bacterial by-products. Plaque adheres tenaciously at the points of irregularity or discontinuity, e.g., on rough calculus surfaces, at the gum line and the like. Besides being unsightly, plaque is implicated in the occurrence of gingivitis and other forms of periodontal disease.

A wide variety of antibacterial agents have been suggested in the art to retard plaque formation and the oral infection and dental disease associated with plaque formation. For example, bis-biguanide compounds such as chlorhexidine are well known to the art for their antibacterial activity and have been used in oral compositions to counter plaque formation by bacterial accumulation in the oral cavity. However, it is also well known that bis-biguanide compounds, when used as dental antiplaque agents cause unsightly staining of teeth. Many procedures have been proposed by the art to reduce such tooth staining: U.S. Pat. Nos. 3,925,543, 3,934,002, 3,937,807, 4,051,234, 4,080,441, 4,256,931, 4,273,759 and 4,886,658. However, the presence of bis-biguanide compounds in dentifrice compositions containing conventional ingredients such as abrasives, anionic surfactants and flavorants which are necessary for adequate cleaning and palatability of the dentifrice, these ingredients are normally incompatible with bis-biguanide compounds, and tend to diminish the bioavailability of such compounds necessary for antiplaque efficacy.

U.S. Pat. No. 5,958,381 discloses a dentifrice product capable of delivering a bis-biguanide antibacterial agent without bioavailability limitation and with limited tooth staining. U.S. Pat. No. 5,958,381 discloses a dual component bis-biguanide containing dentifrice composition in which the first component contains a bis-biguanide antibacterial agent and the second component contains an abrasive such as silica or alumina normally incompatible with the bis-biguanide. Undiminished antibacterial efficacy with minimal staining is achieved when the components which are physically separated prior to use are mixed upon tooth brushing application. However, subsequently a problem has been found to exist with the dual component composition in that the packaged dentifrice has been found to lack sufficient shelf stability for commercial acceptance.

SUMMARY OF THE INVENTION

The present invention encompasses a dual component dental composition having improved shelf stability which when applied to teeth contains a combination of a bis-biguanide compound, an abrasive and other ingredients normally incompatible with the bis-biguanide compound whereby reduction of plaque is accomplished during tooth brushing with substantially less staining of teeth that normally accompanies the use of dental compositions containing bis-biguanide compounds.

The present invention is based upon the discovery that when the separately maintained bis-biguanide compound containing dental gel component of U.S. Pat. No. 5,958,381 is prepared with a cellulose polymer thickener instead of polyoxyethylene/polyoxypropylene block copolymer as disclosed in U.S. Pat. No. 5,958,381, improved shelf stability is attained with undiminished antiplaque efficacy and limited staining when the teeth are brushed with the combined components.

DESCRIPTION OF THE PREFERRED EMBODIMENTS

In the practice of the present invention the dental gel component containing the bis-biguanide ingredient is prepared using a vehicle containing a safe and effective amount of the bis-biguanide compound such as chlorhexidine in a suitable pharmaceutically acceptable vehicle in which a cellulose polymer is used as the thickening agent.

The bis-biguanide compounds useful in the practice of the present invention are known to the art and a disclosure of such compounds may be found in U.S. Pat. No. 4,886,650 (columns 2–3) which disclosure is herewith incorporated by reference. A bis-biguanide compound preferred for use in the present invention is di($N_1,N_1$'-p-chlorophenyldiguanido-$N_5$, $N_5$')hexane (chlorhexidine) and water soluble salts thereof, including the digluconate and the diacetate salts, especially the digluconate salts. Other salts include the dipropoonate, the diformate, the dilactate, the dihydrochloride, the dihydrofluoride, the dihydrobromide, the sulfate, the phosphate, the succinate, the pivalate, the citrate, the tartrate and the maleate. Other suitable bis-biguanide compounds include hexetidine, octenidine and alexidine.

The bis-biguanide compounds are incorporated in gel component of the present invention at about 0.001% to about 4% by weight of the gel and preferably about 2%.

The gel component prepared is using a vehicle which contains water, humectant, nonionic surfactant and thickener. The humectant is generally a mixture of humectants, such as glycerin, sorbitol and a polyethylene glycol of a molecular weight in the range of 200–1000, but other mixtures of humectants and single humectants may also be employed. The humectant content is in the range of about 10% to about 50% by weight and preferably about 10–30% by weight. The water content is in the range of about 10 to about 80% by weight.

Cellulose polymer thickeners useful in preparing a stable vehicle for the bis-biguanide containing gel component of the present invention includes hydroxyethylpropylcellulose, hydroxybutyl methyl cellulose, hydroxypropyl methyl cellulose, and hydroxyethyl cellulose sodium carboxymethyl cellulose. The cellulose polymer thickener may be incorporated in the gel component of the present invention at a concentration of about 1.0 to about 6% by weight and preferably about 3 to about 5% by weight.

A surfactant is incorporated in the gel component to provide foaming properties. The surfactant is preferably nonionic and is included in the gel component in amounts up to about 3% and preferably from about 0.05% to about 2% by weight of the composition.

Examples of suitable nonionic surfactants for use in the present invention include condensates of sorbitan esters of fatty acids with ehtylene oxide (polysorbates) such as sorbitan mono-oleate with from about 20 to about 60 moles of ethylene oxide. A particularly preferred polysorbate is Polysorbate 20, polyoxyethylene 20 sorbitan monolaurate.

Additional suitable nonionic surfactants useful in the present invention are the condensation products of an alpha-olefin oxide containing 10 to 20 carbon atoms, a polyhydric alcohol containing 2 to 10 carbon atoms and 2 to 6 hydroxyl groups, and either ethylene oxide or a mixture of ethylene oxide and peropylene oxide. The resultant surfactants are polymers which have a molecular weight in the range from about 400 to about 160, contain from about 40% to about 80% ethylene oxide by weight and have an alpha-olefin oxide to polyhydric alcohol mole ratio in the range from about 1:1 to about 1:3, respectively. Other nonionic surfactants useful in the present invention include condensates of sorbitan esters of fatty acids with polyethylene glycol such as sorbitan isostearate condensed with polyethylene glycol.

The paste component of the present invention in which an abrasive material is included, is generally a paste prepared using a vehicle which contains water, humectant, nonionic surfactant and thickener. The humectant is generally a mixture of humectants, such as glycerin, sorbitol and a polyethylene glycol of a molecular weight in the range of 200–1000, but other mixtures of humectants and single humectants may also be employed. The humectant content is in the range of about 10% to about 80% by weight and preferably about 10–30% by weight. The water content is in the range of about 10 to about 30% by weight.

Thickeners which may be used in the preparation of the abrasive paste component include natural and synthetic gums such as carrageenan (Irish moss), xanthan gum and sodium carboxymethyl cellulose, starch, polyvinylpyrrolidone, hydroxyethylpropylcellulose, hydroxybutyl methyl cellulose, hydroxypropyl methyl cellulose, and hydroxyethyl cellulose. Hydroxyethyl cellulose is the preferred thickener for use in preparing the paste component. The thickener may be incorporated in the abrasive containing dentifrice component of the present invention at a concentration of about 0.1 to about 3% by weight and preferably about 0.3 to about 1.5% by weight.

By using a cellulose polymer thickener in the gel and synthetic gum in the paste component it has been determined that the force required to actuate the dual gel and paste components is substantially reduced as compared to similar dual component compositions in which thickeners of different compositions were used to prepare the individual components.

A surfactant is incorporated in the abrasive paste component to provide foaming properties. The surfactant is preferably nonionic, and is included in the abrasive dentifrice component in amounts up to about 3%, and preferably from about 0.05% to about 2% by weight of the composition.

Examples of suitable nonionic surfactants for use in the present invention include condensates of sorbitan esters of fatty acids with ethylene oxide (polysorbates) such as sorbitan mono-oleate with from about 20 to about 60 moles of ethylene oxide. A particularly preferred polysorbate is Polysorbate 20, polyoxyethylene 20 sorbitan monolaurate.

Additional suitable nonionic surfactants useful in the present invention are the condensation products of an alpha-olefin oxide containing 10 to 20 carbon atoms, a polyhydric alcohol containing 2 to 10 carbon atoms and 2 to 6 hydroxyl groups, and either ethylene oxide or a mixture of ethylene oxide and propylene oxide. The resultant surfactants are polymers which have a molecular weight in the range from about 400 to about 1600, contain from about 40% to about 80% ethylene oxide, by weight, and have an alpha-olefin oxide to polyhydric alcohol mole ratio in the range from about 1:1 to abut 1:3, respectively. Other nonionic surfactants useful in the present invention include condensates of sorbitan esters of fatty acids with polyethylene glycol such as sorbitan diisostearate condensed with polyethylene glycol.

Silica abrasives are the preferred abrasive for preparing the paste component of the present invention. Examples of such silica abrasives include precipitated silicas having a mean particle size of up to about 20 microns, such as Zeodent 115, marketed by J. M. Huber Chemicals Division, Havre de Grace, Maryland 21078, or Sylodent 783 marketed by Davison Chemical Division of W. R. Grace & Company.

Particularly preferred abrasive materials useful in the practice of the preparation of dentifrice compositions in accordance with the present invention include silica gels and precipitated amorphous silica having an oil absorption value as measured by ASTM Rub-Out Method D281 of less than 100 cc/100 g silica and preferably in the range of from about 45 cc/100 g to less than about 70 cc/100 g silica. These silicas are colloidal particles having an average particle size ranging from about 3 microns to about 12 microns, and more preferably between about 5 to about 10 microns and a pH range from 4 to 10 preferably 6 to 9 when measured as a 5% by weight slurry.

Commercially available low oil absorption silica abrasives are marketed under the trade designation Sylodent XWA by Davison Chemical Division of W. R. Grace & Co., Baltimore, Md. 21203. Sylodent 650 XWA, a silica hydrogel composed of particles of colloidal silica having a water content of 29% by weight averaging from about 7 to about 10 microns in diameter, and an oil absorption of less than 70 cc/100 g of silica.

The silica abrasive is present in the oral are compositions of the present invention at a concentration of about 5 to about 50% by weight and preferably about 10 to about 40% by weight.

Fluorine-providing salts having anti-caries efficacy may also be incorporated in the abrasive dentifrice component of the present invention and are characterized by their ability to release fluoride ions in water. Among these materials are alkali metal salts, for example, sodium fluoride, potassium fluoride, sodium fluorosilicate, and sodium monofluorophosphate. It is preferable to employ a fluoride salt to release about 10 to 1500 ppm of fluoride ion in the product mixture.

Any suitable flavoring or sweetening material may also be incorporated in the abrasive containing dentifrice component of the present invention. Examples of suitable flavoring constituents are flavoring oils, e.g., oils of spearmint, peppermint, wintergreen, sassafras, clove, sage, eucalyptus, marjoram, cinnamon, lemon and orange and methyl salicylate. Suitable sweetening agents include sucrose, lactose, maltose, sorbitol, xylitol, sodium cyclamate, perillartine and sodium saccharin. Suitably, flavor and sweetening agents may together comprise from 0.01% to 5% by weight or more of the abrasive containing dentifrice and at such concentrations render the combined gel and dentifrice components with a palatability acceptable to the user.

A striped dentifrice product is obtained in accordance with the practice of the present invention wherein colorants of contrasting colors are incorporated in each of the dentifrice components used in the practice of the present invention, the colorants being pharmacologically and physiologically nontoxic when used in the suggested amounts.

Colorants used in the practice of the present invention include pigments and dyes.

Pigments used in the practice of the present invention include non-toxic, water insoluble inorganic pigments such as titanium dioxide and chromium oxide greens, ultramarine blues and pinks and ferric oxides as well as water insoluble dye lakes prepared by extending calcium or aluminum salts of FD&C # Yellow 15 lake. The pigments have a particle size in the range of 5–1000 microns, preferably 250–500 microns, and are present at a concentration of 0.5 to 3% by weight.

The dyes used in the practice of the present invention are generally food color additive presently certified under the Food Drug & Cosmetic Act for use in food and ingested drugs, including dyes such as FD&C Red #3 (sodium salts of tetraiodofluorescein), FD&C Yellow #5 (sodium slat of 4-p-sulfophenylaxo-B-naphtol-6-monosulfonate), FD&C Green #3 (disodium salt of 4-{[4-(n-ethyl-p-sulfobenzylamino)-phenyl ]-4-hydroxy-2-sulfoniumphenyl)-methylene}-[1-(N-ethyl-N-p-sulfobenzyl)-3,5-cyclohexadienimine], FD&C Blue #1 (disodium salt of disulfonic acid of indigotin) and mixtures thereof in various proportions. The concentration of the dye for the most effective result in the present invention is present in the abrasive containing dentifrice composition in an amount from about 0.0005% to about 2% by weight.

It is preferred that the colorant included in the gel component be a dye and that the colorant included in the abrasive containing dentifrice component be a pigment such as $TiO_2$ and that the pigment be of a different color than the dye included in the gel component.

To prepare the bis-biguanide compound containing gel component of the present invention, the cellulose polymer and humectant are dispersed in a conventional mixer. The bis-biguanide compound, water and color are mixed separately for 10 minutes. The polymer/humectant mixture is then added to the water mixture in a vacuum mixer and mixed for 20–40 minutes under a vacuum mixer in the range of 5 to 100 millimeter of mercury pressure, preferably 15 to 30 mm Hg, providing a homogeneous mixture. The nonionic surfactant is then added to the mixture which is followed by mixing another 10 to 20 minutes under vacuum of 5 to 50 mm Hg. The resultant product is a non-fluid gel.

To prepare the abrasive containing dentifrice component of the present invention, the humectant and the synthetic gum material are dispersed in a conventional mixer until the mixture becomes a slurry which is smooth in appearance, after which water is added. This mixture is heated to 100–150° F. and mixed for 10 to 30 minutes producing a homogeneous gel phase. Sweetener and color are added and mixed for 20 minutes. The mixture is transferred to a vacuum mixer and the abrasive such as a silica abrasive is added and mixed for 10 to 30 minutes at high speed under a vacuum in the range of 5 to 100 millimeter of mercury pressure, preferably 5 to 50 mm Hg, providing a homogeneous mixture. The surfactant and flavor are then added to the mixture which is followed by mixing another 10 to 20 minutes under vacuum of 5 to 50 mm Hg. The resultant product is an abrasive dentifrice paste of a texture like that of normal toothpastes having a pH in the range of 5 to 8, preferably 5.5 to 6.5, e.g., 6, and of satisfactory flavor.

The dual component composition of the present invention is packaged in a suitable dispensing container such as a tube or pump in which the components are maintained physically separated and from which the separated components may be dispensed synchronously. Such containers are known to the art. Examples of suitable pump devices are disclosed in U.S. Pat. No. 4,528,180 and U.S. Pat. No. 5,332,124. Examples of a suitable dispensing tube are disclosed in U.S. Pat. No. 4,487,757 and 4,687,663 wherein the tube is formed from a collapsible plastic web and is provided with a partition within the tube defining separate compartments in which the physically separated components are stored and from which they are dispersed through a suitable dispensing outlet.

The following specific Example illustrates the present invention. The individual gel and paste components described below were prepared by following the procedure described above. The amounts of the various ingredients are by weight unless otherwise indicated. The resultant components were packaged in tubes or other containers provided with means for physical separation of the individual dentifrice components.

EXAMPLE

A gel component designated "Component A" of a dual component bis-biguanide dentifrice composition of the present invention was prepared with the following ingredients.

| Ingredient | Wt. % |
| --- | --- |
| Chlorhexidine digluconate (20%) | 10.0 |
| Hydroxyethyl cellulose | 4.0 |
| Deionized $H_2O$ | 64.50 |
| Glycerin | 20.0 |
| Polysorbate 20 | 1.20 |
| FD&C Blue #1 1% soln. | 0.30 |

Abrasive Dentifrice Component

An abrasive containing component of the dual component dentifrice composition of the present invention was prepared with the following ingredients:

| Ingredients | Wt. % |
| --- | --- |
| Deionized water | 22.714 |
| Glycerin | 21.00 |
| Sorbitol (70% solution) | 20.00 |
| Xanthan gum | 0.60 |
| Sodium Saccharin | 0.80 |
| Polysorbate 20 | 0.80 |
| Sodium fluoride | 0.486 |
| Zeodent 115 | 20.00 |
| Zeodent 165 | 1.50 |
| Sylodent XWA | 10.00 |
| Titanium Dioxide | 0.50 |
| Flavor | 1.60 |

The gel and abrasive paste components prepared above were of extrudable consistency. The pump force required to actuate extrusion of the combined components was 30 lbs as determined by a Force to Actuate test methodology. Ribbons of the two components were extruded synchronously and combined.

By way of contrast when a dual component composition similar to that of the Example was prepared except that 15% by weight Pluronic F127 was used as the thickening agent, the force required to pump actuate dual extrusion of the separated components was found to be 37 lbs or greater.

A simulated shelf-life test was performed by exposing the gel component to a temperature of 60° C. for 3 weeks and then measuring the retention of chlorhexidine levels at the beginning and end of the test. The gel component used in the dual component composition of the Example designated Gel Component A as indicated in Table II below, was found to retain more than 90% of the original Chlorhexidine incorporated in the gel whereas the comparative gel component designated Gel Component B prepared with Pluronic F127, as the thickener in place of hydroxyethyl cellulose, exhibited a retention level of chlorhexidine substantially less than 90%, a retention level of 90% or more being a proxy for acceptable 2-year shelf stability.

TABLE II

Gel Component Shelf Stability at 3 weeks at 60° C.

| Gel Component | Initial Chlorhexidine (%) | After 3 weeks (%) | % Recovery |
|---|---|---|---|
| A | 2.03 | 1.92 | 94.58 |
| B | 2.07 | 1.78 | 85.99 |

What is claimed is:

1. A dual component bis-biguanide antibacterial dental composition having increased shelf stability in which a first component is an extrudable gel containing an orally acceptable vehicle, a cellulose polymer thickener, and a bis-biguanide antibacterial agent compound, in which a silica abrasive is absent, and the second component which is an extrudable paste containing a silica abrasive, in which the bis-biguanide is absent, the first and second components being synchronously extrudible when dispensed for application to the teeth, the first and second components being physically segregated prior to use, the components when mixed upon application to teeth providing improved shelf stability and undiminished antibacterial efficacy to dental tissue, with less staining of teeth than normally occurs with bis-biguanide compound containing dentifrices, said cellulose polymer thickener in said gel substantially reducing the force required to activate the dual gel and paste composition as compared to polyalkylene block copolymer thickeners, said dual components being packaged in and physically separated from each other in a dispensing container from which the separated components are synchronously dispensed when the force is applied to activate the extrusion of the composition from the container outlet.

2. The composition of claim 1 wherein the cellulose polymer is hydroxyethyl cellulose.

3. The composition of claim 1 wherein the cellulose polymer is present in the vehicle of claim 1 at a concentration of about 1% to about 6% by weight.

4. The composition of claim 1 wherein the bis-biguanide is chlorhexidine.

5. The composition of claim 1 wherein the bis-biguanide is present in the gel vehicle at a concentration of about 0.001 to about 4 weight %.

* * * * *